United States Patent [19]

Gordon

[11] Patent Number: 5,512,476
[45] Date of Patent: Apr. 30, 1996

[54] METHOD FOR IN VITRO FERTILIZATION OF OOCYTES USING MICROCHAMBERS

[75] Inventor: Jon W. Gordon, New York, N.Y.

[73] Assignee: Mount Sinai School of Medicine of the City University of New York, New York, N.Y.

[21] Appl. No.: 125,084

[22] Filed: Sep. 22, 1993

Related U.S. Application Data

[63] Continuation of Ser. No. 699,745, May 14, 1991, abandoned.

[51] Int. Cl.⁶ .............................. A61D 19/00; C12N 5/00
[52] U.S. Cl. ..................... 435/240.26; 600/33; 600/34; 600/35
[58] Field of Search ........................... 435/172.2, 240.26; 600/33, 34, 35

[56] References Cited

U.S. PATENT DOCUMENTS 4,725,579 2/1988 Jones, Jr. et al. ........................ 514/12

OTHER PUBLICATIONS

Laufer et al. Infertility, Appleton & Lange, Norwalk, CT, (1990) pp. 481–511.
Bavister, B. D. Fertilization of Hamster Eggs In Vitro at Sperm: Egg Ratios Close to Unity, J. Exp. Zool. (1979) pp. 259–264.

*Primary Examiner*—David M. Naff
*Assistant Examiner*—Deborah K. Ware
*Attorney, Agent, or Firm*—Brumbaugh, Graves, Donohue & Raymond

[57] ABSTRACT

High efficiency in vitro fertilization is achieved when the oocytes to be fertilized are placed in individual, low volume oocyte chambers disposed about the periphery of a microdrop of fertilization medium. A sperm sample, particularly an unfractionated sperm sample, is then placed in the center of the microdrop. Motile sperm tend to move rapidly toward the periphery of the microdrop, thus resulting in an in situ separation of motile from non-motile sperm. Once at the periphery, fertilization by sperm that enter the oocyte chambers is quite facile because of the low volume of the chamber. This method of fertilization can be performed in a culture dish having a plurality of oocyte chambers formed on the interior surface of the base portion of the dish. Each oocyte chamber has a volume which exceeds the volume of an oocyte to be fertilized but is small enough to provide for facile fertilization. In general, the oocyte chamber will have a volume which exceeds the volume of the oocyte by from 800% to 2000%. The oocyte chambers are disposed about the periphery of a central circular region of the dish having a diameter of from 0.5 to 3.0 cm.

16 Claims, 2 Drawing Sheets

METHOD FOR IN VITRO FERTILIZATION OF OOCYTES USING MICROCHAMBERS

This application is a continuation of application Ser. No. 07/699,745, filed on May 14, 1991, now abandoned.

BACKGROUND OF THE INVENTION

This invention relates to a method and apparatus for in vitro fertilization.

Infertility in man and animals can result from many causes and is frequently associated with low sperm counts, low sperm motility and low percentages of viable, motile sperm. One approach to overcoming these problems is in vitro fertilization ("IVF"), i.e., the combination of sperm and oocyte in a controlled and observable environment outside the body.

As presently practiced, in vitro fertilization generally involves the preliminary separation of healthy, motile sperm from less healthy or non-motile sperm by methods such as Percoll gradients or "swim-ups". Laufer et al., in Infertility, Serbel, M. M. eds., Appleton & Lange 1990). Such fractionation steps are carried out in all cases, including those where sperm are normal (e.g., infertility due to pathology in the female's reproductive system). This measure is taken because even normal semen samples contain substantial numbers of immotile or dead sperm and epithelial cells, and these extraneous cells can interfere with interaction of the motile sperm with the eggs. In addition to removal of unwanted sperm, however these sperm fractionation techniques result in substantial losses of motile sperm as well, and thus introduce their own problems which may lead to the failure of in vitro fertilization.

Once the sperm fraction to be used is obtained, the sperm are added to a sample dish containing a small number of oocytes (generally from 1 to 2) in liquid medium. Animal studies have shown that insemination in very small volumes of the liquid medium or "microdrops" is preferable because it maximizes egg:sperm interaction and minimizes the sperm:egg ratio needed for fertilization (Bavister, J. Exp. Zool. 210:259–264 1979). However, in human IVF, microdrops are not used because such drops are subject to rapid fluctuations of pH and/or changes in osmolarity due to evaporation. Thus, standard IVF procedures usually entail insemination of eggs in 2 milliliters of medium. Laufer et al.

These relatively large volumes necessitate insemination with large numbers of sperm ($1-2\times10^5$ or more) in order to assure fertilization. However, when the sperm sample is abnormal or when many eggs are obtained, the loss during fractionation can result in insufficient numbers of motile sperm for subsequent insemination. This problem is particularly severe when the sperm count is low and/or the percentage of motile sperm in the sample is low.

There thus exists a need in the art for an in vitro fertilization technique which provides high fertilization efficiency without a preliminary sperm fractionation step being necessary. It is the object of the present invention to provide a method and apparatus to meet this need.

SUMMARY OF THE INVENTION

In accordance with the invention, high efficiency fertilization is achieved when the oocytes to be fertilized are placed in individual, low volume oocyte chambers disposed about the periphery or at the center of a drop of fertilization medium. A sperm sample, particularly an unfractionated sperm sample, is then placed in the center of the drop or a revised center. Motile sperm tend to move rapidly toward the oocyte chambers in this circumstance, thus resulting in an in situ separation of motile from non-motile sperm. Fertilization by sperm that enter the oocyte chambers is quite facile because of the low volume of the chamber.

This method of fertilization is advantageously performed in a culture dish which is specially designed for this purpose. Such a culture dish has a plurality of oocyte chambers formed on the interior surface of the base portion of the dish. Each oocyte chamber has a volume which exceeds the volume of an oocyte to be fertilized but is small enough to provide for facile fertilization. In general, the oocyte chamber will have a volume which exceeds the volume of the oocyte by from 800% to 2,000%. The oocyte chambers may be disposed about the periphery of a central circular region of the dish having a diameter of from 0.5 to 3 cm., or on a central plateau region.

DETAILED DESCRIPTION OF THE INVENTION

The present invention provides for both separation of sperm and isolation of oocytes within a low volume of fertilization medium in a single-step procedure. The efficiency of this procedure has been demonstrated using a prototype fertilization microchamber as shown in FIG. 1.

Figure 1:
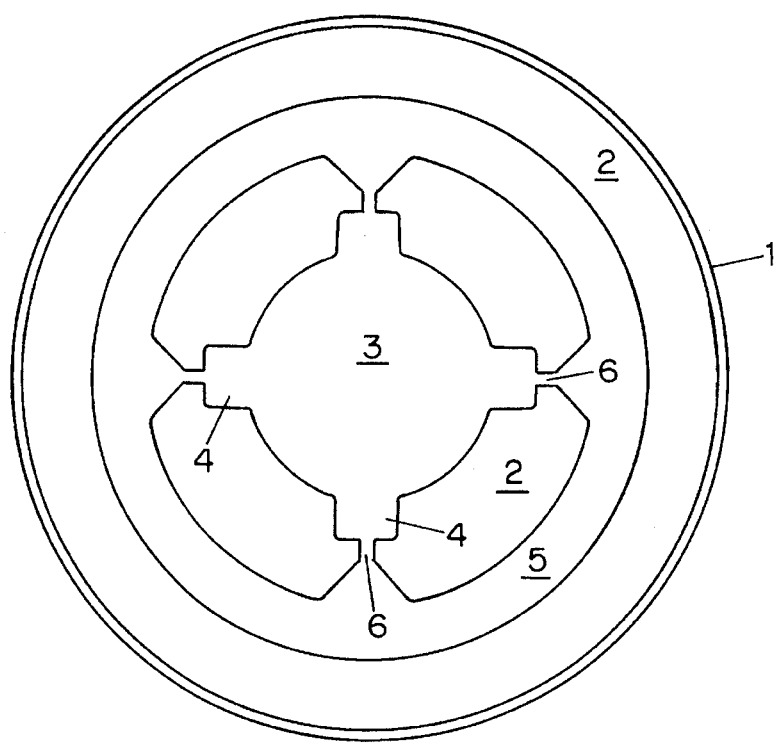
FIG. 1 shows an embodiment of the invention in which the oocyte chambers are formed by shaping the periphery of the microdrop.

In FIG. 1, a culture dish is shown from above. The dish consists of side portion 1 which extends about the entire edge of the dish and a base portion 2. A microdrop of culture medium 3 was placed at the center of the interior surface of the base portion 2 and oocytes chambers 4 were formed by exploiting the adhesive properties of the dish surface to form the microdrop in this shape using a plastic micropipet tip. A ring of culture medium 5 was placed around the microdrop, and channels of medium 6 were formed to connect each oocyte chamber 4 to the ring of culture medium 5. The dimensions of the various portions of the experimental device are shown in Table 1.

TABLE 1

| Dimensions of Experimental Paradigm of FIG. 1 | |
|---|---|
| Diameter of culture dish base portion | 80 mm |
| Diameter of central microdrop | 40 mm |
| Volume of central microdrop | 100 μl |
| Dimensions of oocyte chambers | 150 μm W × 200 μm L |
| Width of outer ring of medium | 10 mm |
| Volume of outer ring of medium | 200 μl |

To test the efficacy of this design, mouse oocytes (having a diameter of about 80 μM) were placed in each of the four oocyte chambers formed in a microdrop of the medium, a sample of unfractionated frozen-thawed mouse sperm was added to the center of the microdrop and an oil drop was placed over the top to maintain the medium in place. Material tended to flow through the channels 6 from the central microdrop 3 to the outer ring 5, and this flow kept the oocytes in place within the oocyte chambers. The results of using this design for in vitro fertilization were a five-fold increase in fertilization efficiency.

The individual construction of a "custom" in vitro fertilization dish for each use is not really practical, both because some skill is involved in creating the oocyte chambers and channels and because the process is time consuming. Further, it was found that imperfectly balanced surface tension between the central microdrop and the outside ring can damage the oocytes. A culture dish suitable for mass production was therefore designed in which the principles embodied in the mouse experiment described above could be more routinely practiced.

Figure 2:
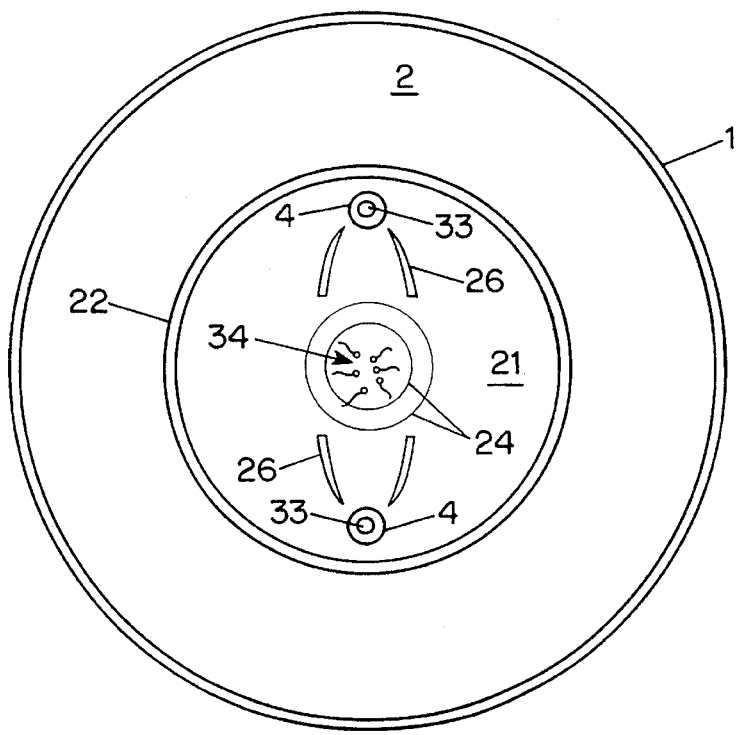
FIG. 2 shows a top view of a culture dish in accordance with the invention.

FIG. 2 shows a top view of a culture dish particularly adapted for use in the invention. In this culture dish there are two oocyte chambers 4 disposed at opposite sides of a circular region 21 and inside a wall member 22 which defines the edge of the microdrop of medium.

It will be understood, however, that the number of oocyte chambers may be greater, with 2 to 60 being the normal range of oocytes available for in vitro fertilization attempt.

The central circular region 21 advantageously has a central depression 31 (FIG. 3) so that a ridge 32 is formed between the center of the central circular region 21 and the oocyte chambers 4. The diameter of the central circular region 21 is advantageously from 0.5 to 30 mm, preferably 10 to 20 mm.

In use, a microdrop of medium is placed within the wall member 22. The volume of the microdrop will depend on the diameter of the central circular region 21, the depth of the central depression 31, if present, and the volume and number of the oocyte chambers 4, but will generally be on the order of 80 to 120 μl. As discussed below, higher volumes can be used if guide members are present to direct the sperm. Oocytes 33 are placed in the oocyte chambers 4 and a sperm sample 34 is placed in the center of the central circular region 21. The central circular region 21 may have rings 24 (FIG. 2) printed on it to help define the volume of sperm to be added. The number of sperm added is generally from 8,000 to 12,000 in volumes of 8–12 μl.

After addition of the sperm, the central circular region 21 may be covered using a top 35 which overlaps the wall member 22. The dish is then allowed to stand for a period of time (usually 10 to 20 hours) to allow healthy, motile sperm to swim to the oocyte chambers at the edge of the central circular region and fertilize the oocytes present therein.

Figure 4:
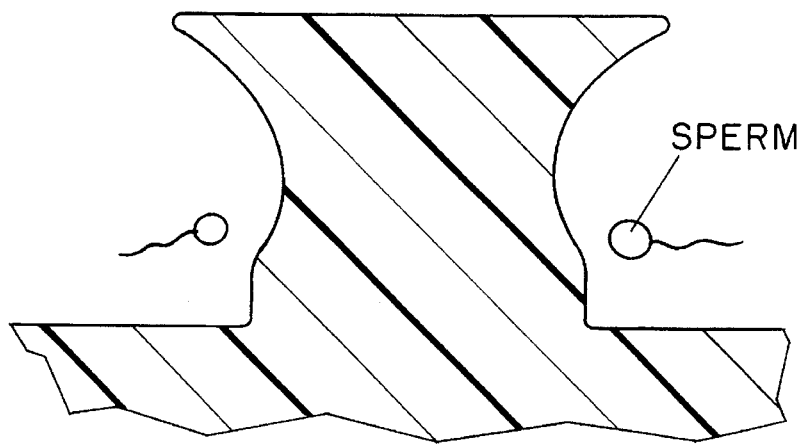
FIG. 4 shows a sectional view through a T-shaped guide member.

The culture dish according to the invention may also include guide members 26 disposed on the surface of the central circular region 21. These guide members tend to direct motile sperm toward those portions of the periphery where oocyte chambers exist and thus enhance the speed and frequency of fertilization. Preferred guide members have T-shaped cross sections (FIG. 4). The use of guide members facilitates the use of larger volumes in the "microdrop" with volumes as high as 1–2 ml being potentially useful.

Figure 3:
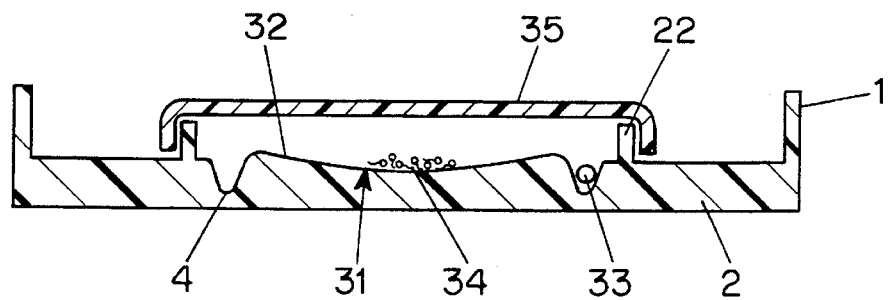
FIG. 3 shows a sectional side view of a culture dish in accordance with the invention.

The oocyte chambers of the invention can be simple depressions, as shown in FIG. 3, or they may have a vortex shape. In the latter case, the oocyte chambers have a top diameter of from 200 to 5,000, preferably 400 to 1,000 microns, a bottom diameter of from 200 to 2,000, preferably from 200 to 500 microns and a depth of from 150 to 1,000, preferably from 150 to 500 microns.

The microchamber configuration shown in FIG. 1 can also be established by forming a raised border on the surface of, e.g. a plastic dish about the periphery of the microdrop. Oocyte chambers can be annexes formed in this raised border or depressions as discussed above.

In addition to the elements discussed above which actively participate in the IVF process the chambers may also include a well around the chamber to provide a source of water vapor to reduce evaporation. The well is not contiguous with the microchamber but would be situated under the cover along with the microchamber.

The method of the present invention is useful for achieving in vitro fertilization of human oocytes as well as oocytes from animals. These oocytes have a variety of sizes, ranging from about 80 to about 150 microns in diameter. For example, human oocytes are generally about 120 microns in diameter, while oocytes from mice and rats are generally about 80 microns in diameter. As used herein, the term "oocyte" may also encompass oocytes together with the surrounding cumulus cells, or small clusters of oocytes which are retrieved together and cannot be separated.

The oocytes to be fertilized are manually placed into oocyte chambers, for example by micropipetting as is normally used to load eggs for standard insemination. The oocyte chambers are sized for the particular species of oocyte to be fertilized. In order to avoid damage to the oocyte and yet obtain efficient fertilization, the volume of the chamber is generally from 800 to 2,000% of the volume of the oocyte. A suitable chamber size for use with a number of species, including man, has dimensions of 200 μ Diameter ×400 μ depth.

The particular medium employed within the culture dish is not critical, and any medium known to be appropriate for a particular species may be used. For example, successful results have been obtained using the human media shown in Table 2.

EXAMPLE 1

Frozen-thawed mouse sperm were used to study the utility of the prototype device as shown in FIG. 1, because most murine sperm fail to survive freezing. In the test, oocytes were zona drilled as described in Gordon et al., J. Exp. Zool. 239, 347 (1986) to assist the few motile sperm to penetrate the oocyte and then placed individually into oocyte chambers formed in a microdrop of the fertilization medium shown in Table 3. A 10 μl sample of frozen-thawed sperm was then deposited in the center of the microdrop. Over five experiments in which the percentage of motile sperm was less than 5%, an average of 65% fertilization (range 53–76%) was achieved.

TABLE 2

| Fertilization Medium for In Vitro Fertilization of Human Oocytes | | |
| --- | --- | --- |
| COMPONENT (mg/L) | F-10 (1x) | Eagle's Medium (1x) |
| INORGANIC SALTS: | | |
| CaCl$_2$ (anhyd.) | — | 200.00 |

TABLE 2-continued

Fertilization Medium for In Vitro Fertilization of Human Oocytes

| COMPONENT (mg/L) | F-10 (1x) | Eagle's Medium (1x) |
|---|---|---|
| $CaCl_2.2H_2O$ | 44.1 | — |
| $CuSO_4.5H_2O^8$ | 0.0025 | — |
| $FeSO_4.7H_2O$ | 0.834 | — |
| KCl | 285.0 | 400.00 |
| $KH_2PO_4$ | 83.0 | — |
| $MgSO_4.7H_2O$ | 152.8 | 200.00 |
| NaCl | 7400.0 | 6800.00 |
| $NaHCO_3$ | 1200.0 | 2200.00 |
| $NaH_2PO_4.H_2O$ | — | 140.00 |
| $Na_2HPO_4.7H_2O$ | 290.0 | — |
| $ZnSO_4.7H_2O$ | 0.0288 | |
| OTHER COMPONENTS: | | |
| D-Glucose | 1100.0 | 1000.00 |
| Hypoxanthine | 4.0 | — |
| Lipoic acid | 0.2 | — |
| Phenol red | 1.2 | 10.00 |
| Sodium pyruvate | 110.0 | |
| Thymidine | 0.7 | |
| AMINO ACIDS: | | |
| L-Alanine | 9.0 | — |
| L-Arginine | — | 17.40 |
| L-Arginine HCl | 211.0 | — |
| $L$-Asparagine.$H_2O$ | 15.01 | |
| L-Aspartic acid | 13.0 | |
| L-Cysteine | 25.0 | |
| L-Cystine | — | 12.00 |
| L-Glutamic acid | 14.7 | |
| L-Glutamine | 146.00 | 292.00 |
| Glycine | 7.51 | |
| L-Histidine | — | 8.00 |
| $L$-Histidine $HCl.H_2O$ | 23.0 | |
| L-Isoleucine | 2.6 | 26.00 |
| L-Leucine | 13.0 | 26.00 |
| L-Lysine | — | 29.20 |
| L-Lysine HCl | 29.0 | — |
| L-Methionine | | 7.50 |
| L-Phenylalanine | | 16.50 |
| L-Threonine | | 24.00 |
| L-Tryptophane | | 4.00 |
| L-Tyrosine | | 18.00 |
| L-Tyrosine (Disodium salt) | — | |
| L-Valine | | 23.50 |
| VITAMINS: | | |
| Biotin | 0.024 | 1.00 |
| Choline bitartrate | — | 1.00 |
| Choline chloride | 0.698 | 1.00 |
| Folic acid | 1.32 | 1.00 |
| i-Inositol | 0.541 | 2.00 |
| Nicotinamide | | 1.00 |
| Pyridoxal HCl | | 1.00 |
| Riboflavin | 0.376 | 0.10 |
| Thiamine HCl | 1.00 | 1.00 |
| D-Ca-pantothenate | 0.715 | |
| Niacinamide | 0.615 | |
| Pyrodoxine HCL | 0.206 | |
| Vitamine $B_{12}$ | 1.36 | |

TABLE 3

| | |
|---|---|
| NaCl (Mallinckrodt #7851) | 5.14 grams |
| KCl (Baker #I-3040) | 0.36 grams |
| $KH_2PO_4$ (Mallinckrodt #7100) | 0.16 grams |
| $MgSO_4$—$7H_2O$ (Mallinckrodt #6066) | 0.29 grams |
| $NaHCO_3$ (Fischer #S-233) | 2.11 grams |
| Na Pyruvate (Schwartz-Mann #904144) | 0.04 grams |
| Glucose (Fischer #D-16) | 1.00 grams |
| Penicillin G, K salt (Schwartz-Mann #4049) | 0.75 grams |

TABLE 3-continued

| | |
|---|---|
| Streptomycin sulfate (Schwartz-Mann #3242) | 0.05 grams |
| Weigh these ingredients into a flask, add 995 ml double distilled $H_2O$, and stir until dissolved. Then add | |
| Sodium lactate 60%, Pfanstiehl Labs | 3.68 ml |
| Phenol red, 1% solution (Difco #5358–59) | 1.00 ml |
| To this add 3 grams/liter crystalline bovine serum albumin (Pentex #81-001-3) and stir until dissolved. This medium is filtered through an 0.22 micron Millipore filter for sterilization and may be stored at 4° C. | |

For comparison zona drilled mouse oocytes were exposed to the same volume of frozen-thawed sperm in a 2 ml tissue dish. In this environment, a fertilization rate of only 3% was observed, probably because the many immotile sperm blocked access to the oocyte.

The improved efficiency of in vitro fertilization in the culture dish of the invention makes it feasible to preserve valuable mouse strains such as transgenic lines by sperm cryopreservation. Thus, the present invention may prove a valuable tool in the management of valuable animal strains.

EXAMPLE 2

Sperm from vasectomized male mice that had proven sterile for more than six months were tested in a shaped microdrop as shown in FIG. 1. A total of 30 oocytes were placed in the oocyte chambers and a 10 μl sample of unfractionated sperm was added. The fertilization medium was that shown in Table 3.

In two experiments, the fertilization efficiency was 100%, including one experiment in which very few free swimming sperm were present. In contrast, only 7% of oocytes were fertilized using the same sperm samples when $10^6$ motile sperm were added to a 2 ml dish of culture medium.

These results indicate that the present invention can improve fertilization efficiency in cases where the percentage of motile sperm is very low, i.e. <10%. The invention may prove especially useful in clinical situations such as a congenital absence of the vas deferens or failed vasectomy repair. Further, because fractionation is unnecessary, use of the present invention can be used to simplify "routine" in vitro fertilization.

EXAMPLE 3

The microchamber of FIG. 1 was used to inseminate oocytes with a sperm sample obtained from a human patient with congenital absence of the vas deferens. After recovery and washing, this sample had only $1 \times 10^6$ sperm with approximately 5% motility and was grossly contaminated with blood. The washed sample without fractionation was used to inseminate 2 oocytes in the microchamber and the remainder of the sample was fractionated using the percoll technique.

After percoll fractionation, no motile sperm were recovered for insemination of oocytes not placed in the microchamber. However, 1 of 2 eggs (50%) in the microchamber were fertilized with the unfractionated preparation and an embryo transfer was accomplished.

EXAMPLE 4

In other studies standard inseminations have been carried out by loading human eggs in the microchamber of FIG. 1. Sperm were either washed or diluted and added directly to the chambers, and the fertilization rates were compared to normal control inseminations in 2 ml dishes following the "swim-up" procedure. In one patient with $80 \times 10^6$ motile sperm in the ejaculate, the sperm were simply diluted and placed in the microchamber. In the control, 2 washes followed by swim up was performed, a process requiring nearly 2 hours and resulting in significant sperm loss. Results were better in the microchamber (2/4 eggs fertilized) then in the control (1/6 fertilized) thus showing that the microchamber can eliminate the time, expense and sperm loss associated with washing and fractionation.

In several additional experiments, sperm were washed and used in the microchamber without fractionation. Fertilization rates have been the same in the microchamber (9/28, 32%) as in control dishes (15/56, 27%), again showing that the microchamber eliminates the need for fractionation.

Figure 5:
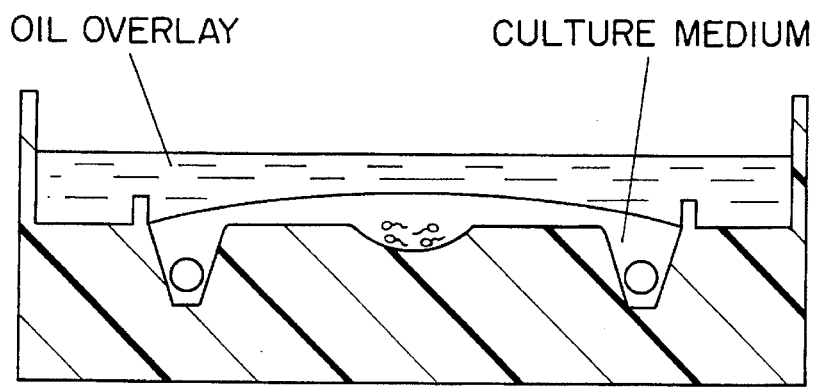
FIG. 5 shows a sectional side view of a culture dish in accordance with the invention.

The foregoing discussion and examples sets forth basic parameters for the method and apparatus of the invention. It will be apparent, however, that other configurations could also be employed. For example, as shown in FIG. 5, a culture dish having one or more oocyte chambers 4 disposed on a central plateau region 51 surrounded by an annular well 52 into which sperm are loaded could also be used in the method of the invention. The central plateau 51 advantageously may have a surface level which is below the interior surface of the base portion.

I claim:

1. A method for achieving in vitro fertilization of an oocyte comprising the steps of (a) placing a drop of fertilization medium in a container;

(b) causing said drop to be shaped such that a portion of the drop is contained within at least one oocyte chamber, the portion of the drop within said at least one chamber being less than the volume of the entire drop both inside and outside said at least one chamber, said chamber volume exceeding the volume of the oocyte by from 800% to 2000%;

(c) causing said oocyte chamber to be formed and positioned in relation to the remainder of said drop such that sperm of normal motility, when placed in said drop remote from said chamber, will tend to congregate in the vicinity of the oocyte chamber and permit contact between an oocyte contained in said chamber and said sperm;

(d) placing an oocyte to be fertilized in said at least one oocyte chamber;

(e) placing a sample of sperm into said drop at a location remote from said at least one oocyte chamber;

(f) allowing said sperm to remain in said drop for a period of time sufficient for sperm of normal motility to congregate in the vicinity of said at least one oocyte chamber; and (g) allowing the oocyte to be fertilized by the sperm and recovering the fertilized oocyte from the oocyte chamber.

2. A method according to claim 1, wherein the drop has a diameter of from 0.5 to 3 cm.

3. A method according to claim 2, wherein the sperm are not fractionated prior to being placed in said drop at a location remote from said at least one oocyte chamber.

4. A method according to claim 1, wherein the sperm are not fractionated prior to being placed in said drop at a location remote from said at least one oocyte chamber.

5. A method according to claim 1, wherein said container comprises a culture dish for in vitro fertilization having a base portion and a side portion, wherein the base portion of the dish has disposed on the interior surface thereof a plurality of oocyte chambers, each having a volume which exceeds the volume of an oocyte to be fertilized by from 800% to 2000% and wherein said oocyte chambers are disposed about the periphery of a central region having a diameter of from 0.5 to 3.0 cm.

6. A method according to claim 5, wherein the oocyte chambers are depressions formed in the interior surface of the base portion of the dish.

7. A method according to claim 6, wherein the central region has a depression at its center such that the depth of a liquid placed in the central region is greater at the center than at the periphery.

8. A method according to claim 6, wherein guide members are formed on the interior surface of the base portion of the dish, said guide members being positioned so that they tend to direct motile sperm placed in the central region to swim toward the oocyte chambers.

9. A method according to claim 8, wherein the central region has a depression at its center such that the depth of a liquid placed in the central region is greater at the center than at the periphery.

10. A method according to claim 8, wherein the oocyte chambers are vortex-shaped.

11. A method according to claim 10, wherein the oocyte chambers have a top diameter of from 200 to 5000 microns, a bottom diameter of from 200 to 2000 microns and a depth of from 150 to 1000 microns.

12. A method according to claim 11, wherein the central region has a depression at its center such that the depth of a liquid placed in the central region is greater at the center than at the periphery.

13. A method according to claim 5, wherein the oocyte chambers have a diameter of about 200 μm and a depth of about 400 μm.

14. A method according to claim 1, wherein said container comprises a culture dish for in vitro fertilization having a base portion and a side portion wherein the base portion has disposed on the interior surface thereof an annular well region defining a central plateau, said plateau having a surface level below the interior surface of the base portion and wherein one or more oocyte chambers are formed on the central plateau, each oocyte chamber having a volume which exceeds the volume of an oocyte to be fertilized by from 800% to 2000%.

15. A method according to claim 14, wherein the oocyte chambers are depressions formed in the interior surface of the base portion of the dish.

16. A method according to claim 14, wherein the oocyte chambers have a diameter of about 200 μm and a depth of about 400 μm.

* * * * *